(12) United States Patent
Liu et al.

(10) Patent No.: US 8,685,956 B2
(45) Date of Patent: Apr. 1, 2014

(54) COMPOSITIONS AND METHODS FOR REDUCING THE RISK OF AGENT-INDUCED LIVER TOXICITY

(75) Inventors: Hong-Hsing Liu, Santa Clara, CA (US); Gary Allen Peltz, Redwood City, CA (US); Guochun Liao, Belmont, CA (US); Timothy Alan Garrow, Mahomet, IL (US)

(73) Assignees: The Board of Trustees of The University of Illinois, Urbana, IL (US); The Board of Trustees of The Leland Stanford Junior University, Palo Alto, CA (US)

( * ) Notice: Subject to any disclaimer, the term of this patent is extended or adjusted under 35 U.S.C. 154(b) by 22 days.

(21) Appl. No.: 13/395,736

(22) PCT Filed: Sep. 16, 2010

(86) PCT No.: PCT/US2010/049093
§ 371 (c)(1),
(2), (4) Date: Mar. 13, 2012

(87) PCT Pub. No.: WO2011/035005
PCT Pub. Date: Mar. 24, 2011

(65) Prior Publication Data
US 2012/0172324 A1     Jul. 5, 2012

Related U.S. Application Data

(60) Provisional application No. 61/243,062, filed on Sep. 16, 2009.

(51) Int. Cl.
*A61K 31/33* (2006.01)

(52) U.S. Cl.
USPC .......................................................... 514/183

(58) Field of Classification Search
USPC .......................................................... 514/183
See application file for complete search history.

(56) References Cited

U.S. PATENT DOCUMENTS

| 4,801,579 | A | * | 1/1989 | Rainer et al. ................ 514/5.5 |
| 5,428,063 | A | | 6/1995 | Barak et al. |
| 2006/0128657 | A1 | | 6/2006 | Messadek |
| 2008/0200533 | A1 | | 8/2008 | Krishnan |

FOREIGN PATENT DOCUMENTS

EP     2011491 A1     1/2009

OTHER PUBLICATIONS

James et al, "Acetaminophen-Induced Hepatotoxicity", Drug Metabolism and Disposition, Dec. 2003, vol. 31, No. 12, pp. 1499-1506.*
The International Search Report and Written Opinion dated May 30, 2011.

(Continued)

*Primary Examiner* — Elli Peselev
(74) *Attorney, Agent, or Firm* — Thomas|Horstemeyer, LLP (57) ABSTRACT

The present disclosure relates generally to a pharmaceutical compositions and methods of reducing acetaminophen-induced liver toxicity. The disclosure includes pharmaceutical compositions including acetaminophen and one or more components selected from S-adenosylhomocysteine (SAH), S-methylmethionine (SMM), or a pharmaceutically acceptable salt thereof. The disclosure also relates to methods of reducing acetaminophen-induced liver toxicity in a subject by administering or co-administering one or more of S-adenosylhomocysteine (SAH), S-methylmethionine (SMM), or a pharmaceutically acceptable salt thereof, with acetaminophen to a subject.

11 Claims, 3 Drawing Sheets

(56) References Cited

OTHER PUBLICATIONS

Seri, et al., "Effects of S-Methylmethionine (Vitamin U) on Experimental Nephrotic Hyperlipidemia," Medical Chemistry and Pathology Sections, Central Research Laboratory, Kaken Chemical Co. Ltd., Tokyo, Japan, pp. 1517-1520, 1979.

Seri, et al., "Hypolipidemic Effects of S-Methylmethionine (Vitamin U) Using Various Experimental Procedures," Medical Chemistry and Pathology Sections, Central Research Laboratory, Kaken Chemical Co. Ltd., Tokyo, Japan, pp. 1694-1703, 1980.

Nakamura, et al., "Hypolipidemic Effect of L-Form S-Methylmethionine Sulfonium Chloride in Man," Department of Internal Medicine, Institute of Constitutional Medicine, Kumamoto University, Kumamoto (Japan), pp. 725-729, 1981.

Liu, et al., "An Integrative Genomic Analysis Identifies Bhmt2 as a Diet-Dependent Genetic Factor Protecting Against Acetaminophen-Induced Liver Toxicity," Genome Research, Nov. 18, 2009, pp. 28-35.

* cited by examiner

COMPOSITIONS AND METHODS FOR REDUCING THE RISK OF AGENT-INDUCED LIVER TOXICITY

CROSS-REFERENCE TO RELATED APPLICATION

This application is the 35 U.S.C. §371 national stage of PCT Application "Compositions and Methods for Reducing the Risk of Agent-Induced Liver Toxicity," having serial number PCT/US2010/049093, filed on Sep. 16, 2010. This application claims priority to and the benefit of U.S. Provisional Application No. 61/243,062, filing date Sep. 16, 2009, which is entirely incorporated herein by its reference.

STATEMENT REGARDING FEDERALLY SPONSORED RESEARCH OR DEVELOPMENT

This invention was made with Government support under contract GM068885 awarded by the National Institutes of Health. The Government has certain rights in this invention.

BACKGROUND

Acetaminophen (APAP) is the most widely used analgesic in the United States. It is a safe and effective drug when administered appropriately. However, an acute overdose causes liver damage by inducing localized centrilobular cell death (see Bessems, J. G. et al., 2001, *Crit. Rev Toxicol* 31: 55-138; and James, L. P. et al., 2003, *Drug Metab Dispos* 31: 1499-1506). Because of the widespread use and low therapeutic index of acetaminophen, acetaminophen toxicity has become the most frequent cause of acute liver failure (see Perkins, J. D. 2006, *Liver Transpl* 12: 682-683).

SUMMARY

Embodiments of the present disclosure relates generally to co-formulation or co-administration of acetaminophen and one or more other chemicals for preventing and reducing the risk of acetaminophen-induced liver toxicity. In particular, the present disclosure relates generally to a co-formulation or co-administration of acetaminophen with one or more chemicals that are metabolites or their derivatives in the methionine and glutathione biosynthesis pathways, for protection against acetaminophen-induced liver toxicity. In an embodiment, the formulation may comprise acetaminophen and diet supplements such as S-methylmethionine (SMM). The present disclosure also encompasses methods of providing pain or fever relief with protection against acetaminophen-induced liver injury with the formulations described herein. Embodiments of the present disclosure also include co-formulation or co-administration of an agent and one or more other chemicals for reducing agent-induced liver toxicity via depletion of glutathione.

An illustrative embodiment of a composition, among others, comprises, consists essentially of, or consists of: acetaminophen and one or more components chosen from S-adenosylhomocysteine (SAH), S-methylmethionine (SMM), cystine, betaine, or a pharmaceutically acceptable salt.

Embodiments of the present disclosure can be in the form of caplet, tablet, capsule, or liquid suspension, for example. Embodiments of the present disclosure can be a pharmaceutical composition including a composition as described herein.

An illustrative embodiment of a method of reducing acetaminophen-induced liver toxicity in a subject, among includes, administering or co-administering one or more of S-adenosylhomocysteine (SAH), S-methylmethionine (SMM), cystine, betaine, or a pharmaceutically acceptable salt, with acetaminophen to a subject.

An illustrative embodiment of a method of reducing acetaminophen-induced liver toxicity in a subject, among includes, administering or co-administering an agent that inhibits homocysteine S-methyltransferase 2 with acetaminophen to the subject.

An illustrative embodiment of a method of reducing acetaminophen-induced liver toxicity in a subject, among includes, administering or co-administering a Bhmt2 substrate with acetaminophen to the subject.

An illustrative embodiment of a composition, among comprises, consists essentially of, or consists of: acetaminophen and one or more components chosen from a chemical that is a metabolite or their derivative in the methionine and glutathione biosynthesis pathways.

An illustrative embodiment of a composition, among includes, an agent that causes liver toxicity via depletion of glutathione and one or more components chosen from S-adenosylhomocysteine (SAH), S-methylmethionine (SMM), cystine, betaine, or a pharmaceutically acceptable salt. The agent can include, but is not limited to, Thiomersal, Troglitazone, bromfenac, trovafloxacin, ebrotidine, nimesulide, nefazodone, ximelagatran and pemoline.

An illustrative embodiment of a method of reducing agent-induced liver toxicity in a subject, among includes, administering or co-administering one or more of S-adenosylhomocysteine (SAH), S-methylmethionine (SMM), cystine, betaine, or a pharmaceutically acceptable salt, with an agent to a subject.

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

Before the present disclosure is described in greater detail, it is to be understood that this disclosure is not limited to particular embodiments described, and the embodiment of the disclosure as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of pharmacy, synthetic organic chemistry, chemistry, and the like, which are within the skill of the art. Such techniques are explained fully in the literature.

The examples herein are put forth so as to provide those of ordinary skill in the art with an illustrative disclosure and description of how to perform the methods and use the compounds disclosed and claimed herein. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like. The phrases "consisting essentially of" or "consists essentially" or the like, when applied to methods and compositions encompassed by the present disclosure refers to compositions like those disclosed herein, but which may contain additional composition components (or method steps). Such additional composition components (or method steps, etc.), however, do not materially affect the basic and novel characteristic(s) of the compositions (or methods), compared to those of the corresponding compositions or methods disclosed herein. "Consisting essentially of" or "consists essentially" or the like, when applied to compositions encompassed by the present disclosure have the meaning ascribed in U.S. Patent law and the term is open-ended, allowing for the presence of more than that which is recited (e.g., trace contaminants, non-active components (e.g., binders, etc), and the like) so long as basic or novel characteristics of that which is recited is not changed by the presence of more than that which is recited, but excludes prior art embodiments.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference.

Definitions

As used herein, "pharmaceutical composition" refers to the combination of an active agent (e.g., acetaminophen and S-adenosylhomocysteine (SAH), S-methylmethionine (SMM), or betaine, and pharmaceutical salts thereof) with a pharmaceutically acceptable carrier. As used herein, a "pharmaceutical composition" refers to a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use.

The term "pharmaceutically acceptable salts" refers to a compound of the present disclosure that can be modified by making acid or base salts thereof. Pharmaceutically acceptable salt refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Examples of pharmaceutically acceptable salts include, but are not limited to, mineral or organic acid salts of basic residues such as amines; and alkali or organic salts of acidic residues such as carboxylic acids.

In the event that embodiments of the present disclosure form salts, these salts are within the scope of the present disclosure. Reference to an agent of any of the formulas herein is understood to include reference to salts thereof, unless otherwise indicated. The term "salt(s)", as employed herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the agents that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

The term "unit dosage form," as used herein, refers to physically discrete units suitable as unitary dosages for human and/or animal subjects, each unit containing a predetermined quantity of a compound calculated in an amount sufficient (e.g., weight of host, disease, severity of the disease, etc) to produce the desired effect in association with a pharmaceutically acceptable diluent, carrier or vehicle while also reducing the risk of acetaminophen-induced liver toxicity. The specifications for unit dosage forms depend on the particular compound employed, the route and frequency of administration, and the effect to be achieved, and the pharmacodynamics associated with each compound in the host.

The terms "effective amount" or "effective dose" as used herein refers to that amount of an embodiment of the present disclosure being administered to relieve pain or fever in a subject, while also reducing the risk of acetaminophen-induced liver toxicity.

As used herein, "treat", "treatment", "treating", and the like refer to acting upon a pain or fever. The improvement or alteration may include an improvement in symptoms or an alteration in the physiologic pathways associated with the pain or fever. "Treatment," as used herein, covers one or more treatments of a disease in a subject (e.g., a mammal, typically a human or non-human animal of veterinary interest), and includes: (a) reducing the pain (b) reducing a fever, and/or (c) relieving the pain or fever.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a pain or fever.

The term "therapeutically effective amount" as used herein refers to that amount of an embodiment of the composition or pharmaceutical formulation being administered that will relieve to some extent one or more of the symptoms of the pain or fever being treated, and/or that amount that will prevent, to some extent, one or more of the symptoms of the pain or fever that the subject being treated has or is at risk of developing.

By "administration" is meant introducing an embodiment of the present disclosure into a subject. Administration can include routes, such as, but not limited to, intravenous, oral, topical, subcutaneous, intraperitoneal, intraarterial, inhalation, vaginal, rectal, nasal, introduction into the cerebrospinal fluid, or instillation into body compartments can be used. A preferred route is oral administration.

As used herein, the term "subject" includes humans, mammals (e.g., cats, dogs, horses, etc.), and other living animals. In particular, the host is a human subject. Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

Discussion:

Embodiments of the present disclosure relates generally to co-formulation or co-administration of acetaminophen and one or more other chemicals for preventing and reducing the risk of acetaminophen-induced liver toxicity. In particular, the present disclosure relates generally to a co-formulation or co-administration of acetaminophen with one or more chemicals that are metabolites or their derivatives in the methionine and glutathione biosynthesis pathways, for protection against acetaminophen-induced liver toxicity. In an embodiment, the formulation may comprise acetaminophen and diet supplements such as S-methylmethionine (SMM). The present disclosure also encompasses methods of providing pain or fever relief with protection against acetaminophen-induced liver injury with the formulations described herein. Embodiments of the present disclosure also include co-formulation or co-administration of an agent and one or more other chemicals for reducing agent-induced liver toxicity via depletion of glutathione.

Acetaminophen is primarily metabolized by sulfation and glucuronidation; the resulting conjugates (APAP-Glu or APAP-Sul) are excreted in urine and bile (see Chen, C. et al. 2003, *Drug Metab Dispos* 31: 798-804). However, Cyp450 enzymes oxidize a small portion of APAP to a reactive quinone metabolite (N-acetyl-p-benzoquinone imine, NAPQI), which covalently binds to cysteine residues in more than 50 different cellular proteins. These adducts are believed to interfere with critical cellular functions, leading to cell death and cell lysis (see James, L. P. et al., 2003, *Drug Metab Dispos* 31: 1499-1506). These defects in turn induce immunological responses that are important in shaping the final outcome (see Harrill, A. H. et al. 2009, *Genome Res*.; Masson, M. J. et al. 2008, *Hepatology* 48: 889-897; and Masubuchi, Y. et al. 2009, *Chem Biol Interact* 179: 273-279).

At therapeutic doses, the reactive quinone metabolite can be efficiently detoxified by conjugation to glutathione (GSH), which plays a major role in detoxifying many hepatotoxic drugs (see Meister, A. et al. 1983, *Annu Rev Biochem* 52: 711-760). However, after a toxic dose of APAP, hepatic glutathione can be depleted by as much as 90%, enabling the reactive intermediates to form adducts with cellular proteins, which can lead to hepatic cell death (see James, L. P. et al., 2003, *Drug Metab Dispos* 31: 1499-1506).

N-acetylcysteine is an effective antidote when administered to patients with severe and ongoing APAP poisoning, and it can act via GSH repletion (see Chun, L. J. et al. 2009, *J Clin Gastroenterol* 43: 342-349). Thus, maintaining hepatic GSH levels at an early stage plays an important role for limiting APAP-induced liver toxicity.

Many factors have been associated with susceptibility to APAP-induced liver injury, including: factors affecting metabolic activation or GSH-mediated detoxification (see Bai, J. et al. 2004, *Mol Cell Biochem* 262: 165-176; Guo, G. L. et al. 2004, *Toxicol Sci* 82: 374-380; Jia, Y. et al. 2005, *Proc Natl Acad Sci U S A* 102: 12531-12536; Welch, K. D. et al. 2005, *Chem Res Toxicol* 18: 924-933), the immune response and cytokine production (see Hogaboam, C. M. et al. 2000, *Am J Pathol* 156: 1245-1252; Ishida, Y. et al. 2002, *FASEB J* 16: 1227-1236; Ishida, Y. et al. 2004, *J Leukoc Biol* 75: 59-67; Liu, Z. X. et al. 2004, *Gastroenterology* 127: 1760-1774), or enzymes regulating apoptosis (see Bhave, V. S. et al. 2008, *Toxicol Appl Pharmacol* 228: 239-246; Limaye, P. B. et al. 2003, *Toxicol Appl Pharmacol* 191: 211-226; Limaye, P. B. et al. 2006, *Hepatology* 44: 379-388). Global analyses of APAP-induced changes in gene expression (see Reilly, T. P. et al. 2001, *Biochem Biophys Res Commun* 282: 321-328) or cellular proteins (see Qiu, Y. et al. 1998, *J Biol Chem* 273: 17940-17953; Ruepp, S. U. et al. 2002, *Toxicol Sci* 65: 135-150; Welch, K. D. et al. 2005, *Chem Res Toxicol* 18: 924-933) have also identified a vast array of other potential mediators. However, none of these factors have actually enabled strategies that can be pro-actively used to prevent APAP-induced liver injury. Thus, there are substantial needs for understanding the mechanism of susceptibility to acetaminophen induced liver toxicity, and developing safe and effective methods to prevent against it.

A panel of inbred mouse strains was studied using an integrated genetic, transcriptional and metabolomic approach in order to better characterize genetic factors affecting susceptibility to APAP-induced liver toxicity.

The liver toxic effect of APAP was assessed by measuring the serum alanine aminotransferase (ALT) activity after a single administration of toxic level (300 mg/kg, intraperitoneal injection) APAP. Significant liver injury developed at 6 hour in all other strains, except SJL/J. The resistant phenotype of SJL/J mice is consistent with the result reported in Welch, K. D. et al. 2005, *Chem Res Toxicol* 18: 924-933.

The transcriptional and metabolomic data of susceptible and resistant strains were analyzed and a subset of genes that could affect susceptibility to APAP-induced liver injury was identified. These results indicate that multiple genetic loci and an interacting network of metabolic factors affect susceptibility to APAP-induced liver injury.

Figure 1:
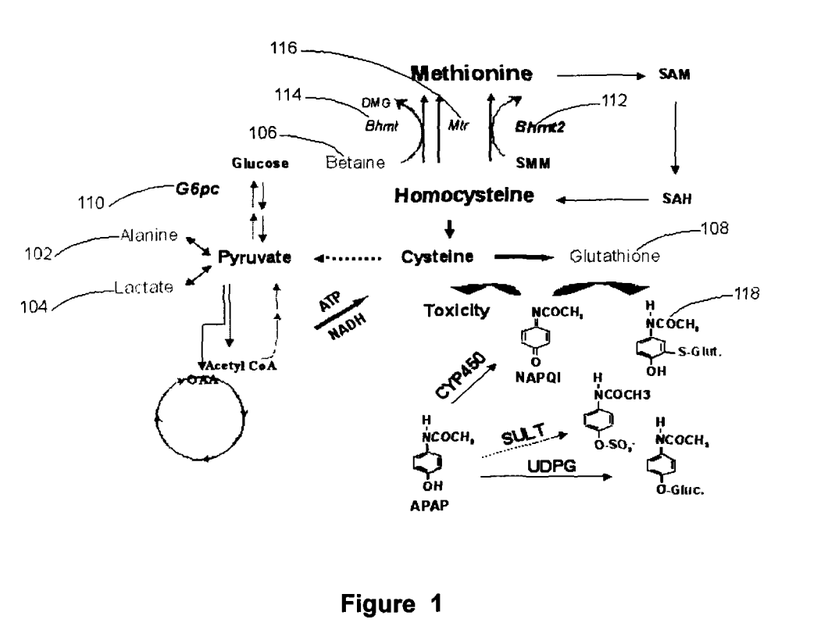
FIG. 1 illustrates metabolic pathways affecting sensitivity to acetaminophen (APAP)-induced hepatotoxicity.

FIG. 1 illustrates the metabolic pathways affecting sensitivity to acetaminophen (APAP)-induced hepatotoxicity. Compared to mouse strains susceptible to APAP-induced liver toxicity, the resistant SJL/J mice had four endogenous metabolites (metabolite 102 (alanine), 104 (lactate), 106 (betaine) and 108 (glutathione) in FIG. 1) with altered abundances, and three enzymes (two are shown in FIG. 1, enzyme 110 (G6 pc) and 112 (Bhmt2)) with altered gene expression after drug exposure.

APAP clearance by sulfation (SULT) or glucuronidation (UDPG), and cytochrome P450 mediated generation of the reactive quinone metabolite (N-acetyl-p-benzoquinone imine, NAPQI) are shown in the right bottom quarter of FIG. 1. NAPQI metabolite can be detoxified by conjugation to glutathione (GSH) to form non-toxic GSH-conjugated NAPQI (metabolite 118 in FIG. 1). Excess NAPQI metabolite would induce toxicity.

Cysteine biosynthesis is the rate-limiting step for glutathione (GSH, 108 in FIG. 1) production.

Cysteine can be converted to pyruvate, which is in equilibrium with alanine (metabolite 102 in FIG. 1) and lactate (metabolite 104 in FIG. 1). An increase in cysteine biosynthesis would explain why alanine and lactate were increased in the resistant mice. Reduced G6 pc (enzyme 110 in FIG. 1) activity will inhibit gluconeogenesis and favor pyruvate breakdown to increase cellular reducing capacity. These metabolic alterations might help SJL/J mice resist an APAP-induced toxic challenge.

FIG. 1 shows three homocysteine methylation enzymes: homocysteine S-methyl transferase (Bhmt, 114 in FIG. 1), 5-methyltetrahydrofolate-homocysteine methyltransferase (Mtr, 116 in FIG. 1), and homocysteine S-methyl transferase 2 (Bhmt2, 112 in FIG. 1).

Bhmt2 is an S-methyl-methionine (SMM)-specific methyltransferase; Bhmt2 has very low activity toward S-adenosylmethionine (SAM), and cannot use betaine as the methyl donor (see Szegedi, S. S. et al. 2008, *J Biol Chem* 283: 8939-8945). Betaine is a required substrate for Bhmt-catalyzed remethylation of homocysteine to form methionine. Sequential steps of SMM- and SAM-dependent methionine/GSH biosynthesis pathways are shown in FIG. 1.

SMM, or S-Methylmethionine, or S-methyl-L-methionine, is a derivative of methionine with chemical formula $C_6H_{14}NO_2S$. It is produced from methionine by the enzyme methionine S-methyltransferase in plants.

SMM is a very ubiquitous and abundant constituent of the free amino acid pool in most flowering plants (see Augspurger, N. R., et al. 2005, *J Nutr* 135: 1712-1717; Mudd, S. H. et al. 1990, *Plant Physiol* 93: 623-630; Paquet, L. et al. 1995, *Canadian journal of botany* 73: 1889-1896) that is universally ingested in the diet. Methionine metabolism in plants differs from that in mammalian organisms by involving SMM, which is the major metabolite used to transport sulfated amino acids. SMM was 80% of the total amount of $^{S}35$-labeled material in phloem of a wheat plant (see ourgis, F. et al. 1999, *Plant Cell* 11: 1485-1498). The absence of the required methyltransferase renders mammals unable to synthesize SMM from L-methionine, yet they clearly obtain SMM in their diet (see Mudd, S. H. et al. 1990, *Plant Physiol* 93: 623-630).

Alterations in Bhmt2 (enzyme 112 in FIG. 1) mRNA and betaine (metabolite 106 in FIG. 1) abundance that favor cysteine production would contribute to resistance to APAP-induced liver injury.

A genetic variation altering Bhmt2 enzyme activity was identified as one of the genetic susceptibility factors of APAP-induced liver toxicity in mice. Four mouse strains, NJ, DBA/2J, C57BL/6J and B10.D2, are susceptible to APAP-induced liver injury. At amino acid position 27, the Bhmt2 proteins in NJ and DBA/2J have Glycine (Gly27) while those in C57BL/6J and B10.D2 have Serine (Ser27). The conversion of Gly27 to Ser27 causes a loss of Bhmt2 enzyme activity in C57BL/6J and B10.D2 mice.

The availability of two inbred strains with allelic variants that eliminate Bhmt2 enzyme activity enabled the hypothesis that Bhmt2 is a susceptibility factor for APAP-induced liver toxicity to be tested in vivo. The effect that co-administration of SAM or SMM, which act on sequential steps in the methionine/GSH biosynthesis pathway, had on APAP-induced liver toxicity in strains with intact or deficient Bhmt2 activity was analyzed. If Bhmt2 affects susceptibility, SMM co-administration should protect against APAP-induced liver damage in strains with intact Bhmt2 enzyme activity, but should not have an effect in strains with inactive Bhmt2 enzyme activity. Since SAM acts just downstream of the Bhmt2-catalyzed step, it should have a protective effect in all strains. Administration of SAM was previously shown to attenuate APAP-induced hepatotoxicity and to preserve hepatic GSH levels in C57BL/6J mice (see Bray, G. P. et al. 1992, *Hepatology* 15: 297-301; Terneus, M. V. et al. 2007, *J Pharmacol Exp Ther* 320: 99-107; Valentovic, M. et al. 2004, *Toxicol Lett* 154: 165-174).

Figure 2:
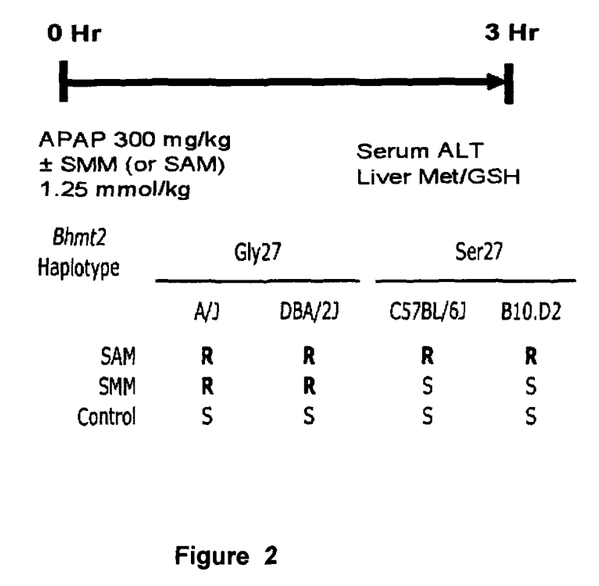
FIG. 2 shows a diagram of an experiment assessing the strain-specific effect of SMM or SAM co-administration on APAP-induced liver toxicity.

FIG. 2 shows a diagram of an experiment assessing the strain-specific effect of SMM or SAM co-administration on APAP-induced liver toxicity. Hepatic glutathione (GSH) and methionine levels and the serum ALT were measured 3 hour after APAP administration to inbred strains. The R and S in the lower panel indicate whether SMM or SAM co-administration should have a protective (Rescue) effect, or not have a beneficial (Susceptible) effect on APAP-induced liver toxicity, respectively. As shown in FIG. 2, co-administration of a Bhmt2-specific substrate (SMM) had a protective effect in strains with active Bhmt2 enzyme (Gly27 allele), but not in strains with inactive (Ser27 allele) enzyme. In contrast, SAM, which affects GSH biosynthesis at a step distal to Bhmt2, had a protective effect in all strains. This indicated that Bhmt2 activity affected sensitivity to APAP-induced liver injury, and its substrate SMM provided strain-dependent protection against APAP-induced liver injury.

Thus, considering the protective effect of SMM, we suggest that SMM can be used as a novel strategy that could be used to prevent APAP-induced liver injury. N-acetylcysteine is the most effective agent for treatment of ongoing APAP-liver toxicity (see Chun, L. J. et al. 2009, *J Clin Gastroenterol* 43: 342-349). However, N-acetylcysteine has a very unpleasant taste and odor, is poorly tolerated after oral administration, and can induce nausea and vomiting. In contrast, SMM does not have these properties, which makes it conceivable that it could be prospectively ingested to prevent APAP-induced liver injury. SMM was originally referred to as 'vitamin U' and has been widely used in Chinese herbal medicine for treatment of gastrointestinal diseases and in clinical studies dating back to the 1950's (see Cheney, G. 1954, *Am J Gastroenterol* 21: 230-250).

In one aspect, the present disclosure is based, in part, on the discovery that homocysteine S-methyltransferase 2 (Bhmt2) affects the susceptibility to acetaminophen-induced liver toxicity in mice. Through an effect on methionine and glutathione biosynthesis, Bhmt2 could utilize its substrate, S-methylmethionine (SMM) to confer protection against acetaminophen-induced liver injury.

Glutathione (GSH) is the major endogenous antioxidant produced by the cells, participating directly in the neutralization of free radicals and reactive oxygen compounds, as well as maintaining exogenous antioxidants such as vitamins C and E in their reduced (active) forms. Through direct conjugation, GSH detoxifies many xenobiotics (foreign compounds) and carcinogens, both organic and inorganic.

GSH is essential for the immune system to exert its full potential as it plays a fundamental role in numerous metabolic and biochemical reactions. Every system in the body can be affected by the state of the GSH system, especially the immune system, the nervous system, the gastrointestinal system, liver and the lungs. In many liver disorders, GSH levels are decreased, such as acetaminophen intoxication, alcohol intoxication and hepatitis. Many drugs and toxins can be detoxified by conjugation with GSH. When the levels of these drugs or toxins, however, exceed the liver concentration of GSH; such components become acutely hepatotoxic.

SMM can be used as a co-formulation agent for hepatic protection for other glutathione-depleting drugs that cause Drug Induced Liver Injury (DILI), such as Thiomersal, an antiseptic and antifungal agent. Many drugs were withdrew from the market because of DILI, such as Troglitazone, bromfenac, trovafloxacin, ebrotidine, nimesulide, nefazodone, ximelagatran and pemoline. For those drugs that GSH depletion is the major reason of DILI, SMM could be a co-formulation agent for rescuing these drugs.

Glutathione deficiency contributes to oxidative stress, which plays a key role in aging and the pathogenesis of many diseases (e.g., kwashiorkor, seizure, Alzheimer's disease, Parkinson's disease, liver disease, cystic fibrosis, sickle cell anemia, HIV, AIDS, cancer, heart attack, stroke, and diabetes). Therefore, SMM can be as a co-formulation agent for increasing GSH level for drugs to treat diseases that cause or are due to GSH deficiency.

Embodiments of the present disclosure provide a composition or a pharmaceutical formulation that can comprise, consist essentially of, or consist of, an agent that causes liver toxicity via depletion of glutathione and one or more components chosen from S-adenosylhomocysteine (SAH), S-methylmethionine (SMM), cystine, betaine, or pharmaceutically acceptable salts of each where applicable. In an embodiment, agents that can or due cause liver toxicity via depletion of glutathione include, but are not limited to, Thiomersal, Troglitazone, bromfenac, trovafloxacin, ebrotidine, nimesulide, nefazodone, ximelagatran and pemoline.

Embodiments of the present disclosure also provide for methods of reducing agent-induced liver toxicity via depletion of glutathione in a subject by administering or co-administering one or more of S-adenosylhomocysteine (SAH), S-methylmethionine (SMM), cystine, betaine, or a pharmaceutically acceptable salt, with an agent to a subject.

Embodiments of the present disclosure provide a composition or a pharmaceutical formulation that can comprise, consist essentially of, or consist of, acetaminophen and one or more chemicals that are metabolites in the methionine and glutathione biosynthesis pathways, including, but not limited to, S-adenosylhomocysteine (SAH), S-methylmethionine (SMM), and betaine, and pharmaceutically acceptable salts of each where applicable.

In an embodiment, the present disclosure provides a pharmaceutical formulation that can comprise, consist essentially of, or consist of, acetaminophen and vitamin U, or SMM. In another embodiment, the present disclosure provides a pharmaceutical formulation that consists essentially of acetaminophen and SAH.

In another embodiment, the present disclosure provides a pharmaceutical formulation that can comprise, consist essentially of, or consist of, acetaminophen and betaine. Other names of betaine include trimethylglycine (also commonly know as TMG) and glycine betaine. Betaine is also in the forms of salt, such as, but not limited to, betaine hydrochloride ("betaine Hcl"), which can be used in place of betaine.

In another embodiment, the present disclosure provides a pharmaceutical formulation that can comprise, consist essentially of, or consist of, of acetaminophen and cystine. Cysteine is potentially toxic and is catabolized in the gastrointestinal (GI) tract and blood plasma, while cystine travels safely through the GI tract and blood plasma, and is promptly reduced to the two cysteine molecules upon cell entry.

Chemicals referred to as the "chemicals of the present disclosure" throughout this disclosure include, for example, cystine, and metabolites in the methionine and glutathione biosynthesis pathways, including for example, but not limited to, S-adenosylhomocysteine (SAH), S-methylmethionine (SMM), and betaine, and pharmaceutically acceptable salts of each where applicable.

Compounds previously shown to attenuate APAP-induced hepatotoxicity include methionine, S-adenosylmethionine (SAM), and cysteine. In some embodiments, a pharmaceutical formulation is provided that can comprise, consist essentially of, or consist of, acetaminophen and a combination of one or more of chemicals of the present disclosure and one or more of compounds previously shown to attenuate APAP-induced hepatotoxicity, for example, methionine, S-adenosylmethionine (SAM), and cysteine.

The present disclosure also provides for a caplet or tablet or capsule or liquid suspension which may comprise, consist essentially of, or consist of an agent (e.g., acetaminophen) and one or more chemicals of the present disclosure.

In an embodiment, the present disclosure provides for a pharmaceutical formulation or a caplet or tablet or capsule or liquid suspension that can comprise, consist essentially of, or consist of, an agent (e.g., acetaminophen) in conjunction with SMM. In another embodiment, the present disclosure provides for a pharmaceutical formulation or a caplet or tablet or capsule or liquid suspension that can comprise, consist essentially of, or consist of, agent (e.g., acetaminophen) and SAH. In another embodiment, the present disclosure provides for a pharmaceutical formulation or a caplet or tablet or capsule or liquid suspension that can comprise, consist essentially of, or consist of, agent (e.g., acetaminophen) and betaine. In another embodiment, the present disclosure provides for a pharmaceutical formulation or a caplet or tablet or capsule or liquid suspension that can comprise, consist essentially of, or consist of, agent (e.g., acetaminophen) and cystine.

In an embodiment, the dosage of acetaminophen per administration is about 100 mg to about 1 g. In one embodiment, when co-administered or co-formulated with agent (e.g., acetaminophen), the dosage of S-methylemthionine (SMM) is about 100 mg to about 20 g.

The present disclosure also provides a method of providing pain or fever relief with protection against agent-induced liver toxicity (e.g., agent can be acetaminophen), which can comprise administering a pharmaceutical formulation or a caplet or a tablet or a capsule or a liquid suspension, which can comprise any one of the formulations described herein to a subject or patient in need of pain or fever relief. In some embodiments, the pharmaceutical formulation or the caplet or tablet or capsule or liquid suspension can be administered at about 4 to 6 hours intervals for a few hours to a number of days, depending upon the desired pain or fever relief and instruction by a physician or pharmacist.

In another embodiment, a kit including a pharmaceutical formulation or a caplet or a tablet or a capsule or a liquid suspension and/or for including performing a method of providing pain or fever relief with protection against agent-induced liver toxicity is provided (e.g., agent can be acetaminophen). An embodiment of the method includes administering any of the compositions, pharmaceutical formulations or caplets or tablets or capsules or liquid suspension, which can comprise any one of the formulations described herein to a patient in need of pain or fever relief and instructions for performing the method.

In another aspect, a kit for performing a method of providing pain or fever relief with protection against agent-induced liver injury is provided (e.g., agent can be acetaminophen), which can comprise co-administering agent (e.g., acetaminophen) and one or more chemicals of the present disclosure (e.g., cystine, and metabolites in the methionine and glutathione biosynthesis pathways, including for example, but not limited to, S-adenosylhomocysteine (SAH), S-methylmethionine (SMM), and betaine, and pharmaceutically acceptable salts of each where applicable) to a patient in need of pain or fever relief and instructions for performing the method.

Figure 3A:
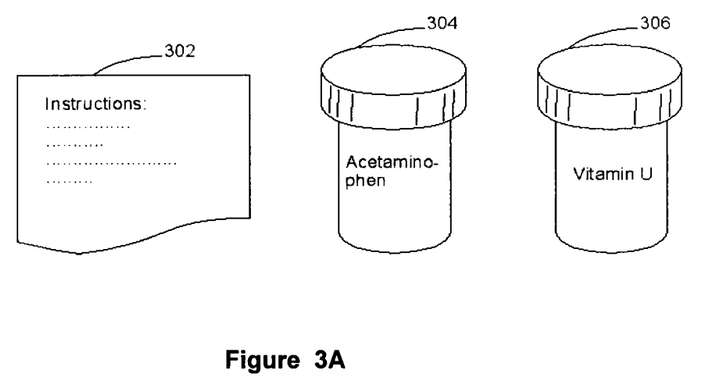
FIG. 3A shows an example of a kit for performing a method of providing pain or fever relief with protection against acetaminophen-induced liver toxicity.

FIG. 3A shows an example of a kit for performing a method of providing pain or fever relief with protection against acetaminophen-induced liver toxicity. The instruction 302 provides the information of co-administration to a patient. The bottle 304 contains acetaminophen tablets or caplets or capsules or liquid suspension from an acetaminophen formulation and from an acceptable acetaminophen brand. The bottle 306 contains vitamin U tablets or caplets or capsules or liquid suspension from a vitamin U formulation and from an acceptable vitamin U brand. In some other embodiments of the present disclosure, the bottle 306 can contain tablets or caplets or capsules that consist of one or more chemicals of present disclosure or a combination of one or more chemicals of present disclosure and one or more of methionine, SAM and cysteine.

Figure 3B:
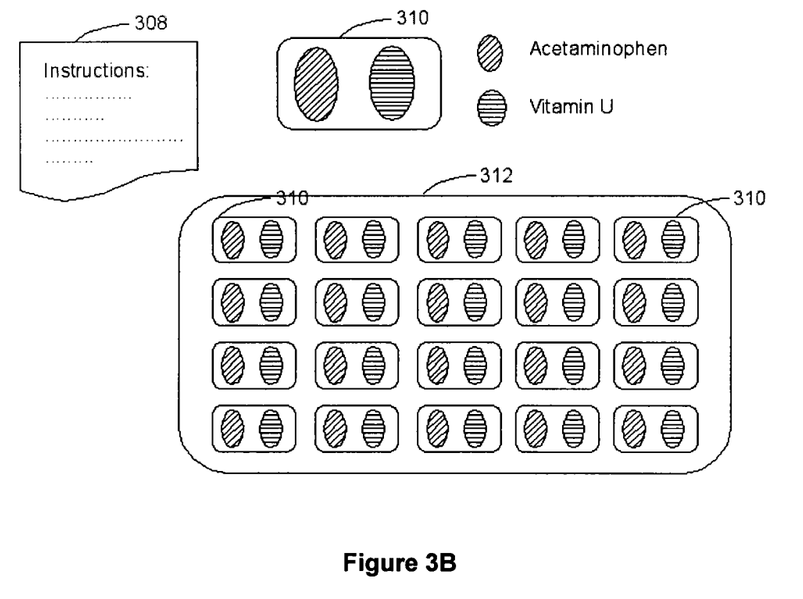
FIG. 3B shows another example of a kit for performing a method of providing pain or fever relief with protection against acetaminophen-induced liver toxicity.

FIG. 3B shows another example of a kit for performing a method of providing pain or fever relief with protection against acetaminophen-induced liver toxicity. The instruction 308 provides the information of co-administration to a patient. The small chamber 310 contains two tablets or caplets or capsules; one is acetaminophen and another is vitamin U. In some embodiments, the small chamber 310 contains more than one tablets or caplets or capsules of acetaminophen; in some embodiments, the small chamber 310 contains more than one tablets or caplets or capsules of vitamin U. In some embodiments, vitamin U in the small chamber 310 can be replaced by one or more chemicals of the present disclosure or a combination of one or more chemicals of the present disclosure and one or more of methionine, SAM, and cysteine. The plate 312 shows a plate with many small chambers 310. In various embodiments of present disclosure, the plate 312 can have various numbers of chambers in each row and each column.

Figure 4:
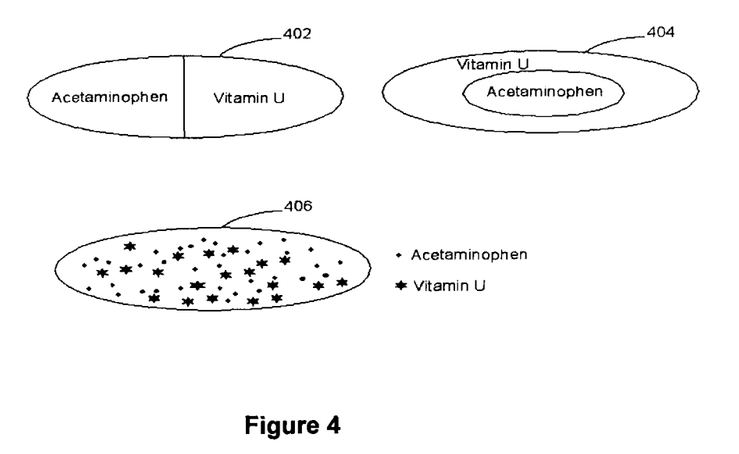
FIG. 4 illustrates examples of co-formulation of acetaminophen and vitamin U.

FIG. 4 illustrates examples of co-formulation of acetaminophen and vitamin U according to one embodiment of the present disclosure.

The tablet or caplet or capsule 402 shows one form of co-formulation where acetaminophen and vitamin U each has one half of the tablet or caplet or capsule. In various embodiments of the present disclosure, vitamin U in 402 can be replaced with one or more chemicals of present disclosure or a combination of one or more chemicals of present disclosure and one or more of methionine, SAM, and cysteine.

The tablet or caplet 404 shows one form of co-formulation where acetaminophen and vitamin U each comprise one layer of the tablet or caplet. In some embodiments, acetaminophen and vitamin U can have more than one layer in a tablet or caplet, and in various order. In various embodiments of the present disclosure, vitamin U in 404 can be replaced with one or more chemicals of present disclosure or a combination of one or more chemicals of present disclosure and one or more of methionine, SAM and cysteine.

The tablet or caplet or capsule 406 shows one form of co-formulation in which small acetaminophen and vitamin U particles are mixed in the tablet or caplet or capsule. In other embodiments, 406 can be a container for liquid suspension that contains the mixture of soluble acetaminophen and vitamin U or small acetaminophen and vitamin U particles. In various embodiments of the present disclosure, vitamin U in 406 can be replaced with one or more chemicals of present disclosure or a combination of one or more chemicals of present disclosure and one or more of methionine, SAM, and cysteine.

Figure 5:
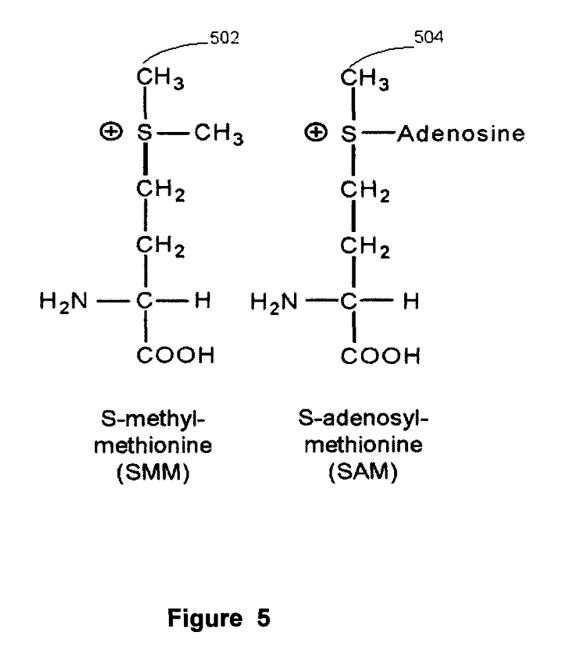
FIG. 5 illustrates the chemical structure of SMM and SAM.

FIG. 5 shows the chemical structure of SMM (502 in FIG. 5), and the chemical structure of SAM (504 in FIG. 5).

SMM has many synonyms, including, but not limited to, Vitamin U, Cabagin U, methylmethionine sulfonium salt, 64382_FLUKA, 64382_SIGMA, methylmethionine sulfonium chloride, methyl-methionine sulphonium chloride, L-methylmethionine sulfonium chloride, DL-methionine methylsulfonium chloride. SMM has many analogs in the form of methylmethionine sulfonium salt, such as, but not limited to, methylmethioninesulfonium bromide (Bromide analog C6H14BrNO2S) and (3-amino-4-hydroxy-4-oxobutyl)-dimethylsulfanium iodide (Iodide analog C6H14INO2S).

Brands of SMM that can be used in the co-formulation or co-administration of the present disclosure include, but are not limited to, Maxwell Nutrition Cabagin U, Stomacin-U, Biotics Research Gastrazyme and Balanceuticals Uterus Care.

Acetaminophen formulations are described in U.S. Pat. Nos. 6,936,601; 6,926,907; 6,924,273; 6,916,788; 6,855,310; 6,852,336; 6,841,544; 6,833,362; 6,828,328; 6,787,164; 6,740,333; 6,702,850; 6,696,066; 6,686,390; 6,642,243; 6,627,234; 6,622,856; 6,613,346; 6,602,518; 6,593,331; 6,586,023; 6,569,439; 6,566,401; 6,566,361; 6,544,548; 6,528,097; 6,524,623; 6,511,982; 6,509,380; 6,492,334; 6,485,747; 6,482,831; 6,479,551; 6,475,526; 6,475,494; 6,458,809; 6,444,665; 6,440,983; 6,429,223; 6,413,512; 6,406,716; 6,391,886; 6,391,337; 6,391,294; 6,384,054; 6,383,527; 6,383,515; 6,375,957; 6,369,084; 6,369,082; 6,355,666; 6,350,467; 6,335,034; 6,309,669; 6,306,842; 6,303,632; 6,284,274; 6,277,384; 6,254,891; 6,245,802; 6,245,357; 6,242,493; 6,225,295; 6,221,377; 6,217,911; 6,217,907; 6,214,386; 6,187,338; 6,162,647; 6,159,500; 6,139,861; 6,127,352; 6,126,967; 6,077,533; 6,077,530; 6,057,347; 6,054,451; 6,048,540; 6,028,222; 6,007,841; 5,998,434; 5,972,916; 5,968,551; 5,965,167; 5,965,166; 5,945,416; 5,942,530; 5,919,826; 5,914,129; 5,897,880; 5,891,801; 5,891,477; 5,872,145; 5,863,922; 5,840,731; 5,837,729; 5,827,852; 5,776,462; 5,773,031; 5,739,139; 5,733,578; 5,724,957; 5,654,334; 5,639,475; 5,612,061; 5,603,959; 5,538,959; RE35,213; 5,474,757; 5,468,482; 5,466,865; 5,458,879; 5,417,980; 5,409,944; 5,409,709; 5,336,691; 5,322,689; 5,296,241; 5,273,759; 5,260,340; 5,238,686; 5,204,118; 5,154,926; 5,100,675; 5,036,097; 5,023,085; 5,011,688; 4,971,960; 4,971,785; 4,829,064; 4,822,781; 4,812,446; 4,794,112; 4,730,007; 4,703,045; 4,478,822; 4,476,115; 4,466,960; 4,460,368; 4,401,665; 4,314,989; 4,307,073; 4,260,629; 4,242,353; 4,237,140; 4,234,601; 4,233,317; 4,233,316; 4,233,315; 4,233,314; 4,233,313; 4,207,340; 4,132,788 and 4,049,803, the disclosures of which are incorporated by reference in their entireties. These acetaminophen formulations can be used in the compositions and methods of the present disclosure.

Brands of acetaminophen which can be used in the compositions and methods of the present disclosure include, but are not limited to, Aceta Elixir, Aceta Tablets, Acetaminophen Uniserts, Actamin, Actamin Extra, Actamin Super2, Aminofen, Aminofen Max, Apacet Capsules, Apacet Elixir, Apacet Extra Strength Caplets, Apacet Extra Strength Tablets, Apacet, Infants', Apacet Regular Strength Tablets, Aspirin Free Anacin Maximum Strength Caplets, Aspirin Free Anacin Maximum Strength Gel Caplets, Aspirin Free Anacin Maximum Strength Tablets, Aspirin-Free Excedrin Caplets2, Banesin, Bayer Select Maximum Strength Headache Pain Relief Formula2, Dapa, Dapa X-S, Datril Extra-Strength, Equate, Excedrin, Feverall, Children's, Feverall, Infants', Feverall Junior Strength, Feverall Sprinkle Caps, Children's, Feverall Sprinkle Caps Junior Strength, Genapap Children's Elixir, Genapap Children's Tablets, Genapap Extra Strength Caplets, Genapap Extra Strength Tablets, Genapap, Infants', Genapap Regular Strength Tablets, Genebs Extra Strength Caplets, Genebs Regular Strength Tablets, Genebs X-Tra, Goody's, Liquiprin Children's Elixir, Liquiprin Infants' props, Neopap, Oraphen-PD, Panadol, Children's, Panadol, Infants', Panadol Junior Strength Caplets, Panadol Maximum Strength Caplets, Panadol Maximum Strength Tablets, Phenaphen Caplets, Redutemp, Snaplets-FR, St. Joseph Aspirin-Free Fever Reducer for Children, Suppap-20, Suppap-325, Suppap-650, Tapanol Extra Strength Caplets, Tapanol Extra Strength Tablets, Tempra, Tempra D.S, Tempra, Infants', Tempra Syrup, Tylenol Arthritis Extended Relief, Tylenol Children's Chewable Tablets, Tylenol Children's Elixir, Tylenol Children's Suspension Liquid, Tylenol Extra-Strength Adult Liquid Pain Reliever, Tylenol Extra Strength Caplets, Tylenol Extra Strength Gelcaps, Tylenol Extra Strength Tablets, Tylenol Infants' props, Tylenol Infants' Suspension props, Tylenol Junior Strength Caplets, Tylenol Junior Strength Chewable Tablets, Tylenol Regular Strength Caplets, Tylenol Regular Strength Tablets, Valorin and Valorin Extra in the United States and Abenol, Actimol Chewable Tablets, Actimol Children's Suspension, Actimol Infants' Suspension, Actimol Junior Strength Caplets, Anacin-3, Anacin-3 Extra Strength, Apo-Acetaminophen, Atasol Caplets, Atasol props, Atasol Forte Caplets, Atasol Forte Tablets, Atasol Oral Solution, Atasol Tablets, Excedrin Caplets2, Excedrin Extra Strength Caplets2, Exdol, Exdol Strong, Panadol, Panadol Extra Strength, Robigesic, Rounox, Tempra Caplets, Tempra Chewable Tablets, Tempra props, Tempra Syrup, Tylenol Caplets, Tylenol Children's Chewable Tablets, Tylenol props, Tylenol Elixir, Tylenol Gelcaps, Tylenol Junior Strength Caplets and Tylenol Tablets in Canada.

The amount of a chemical of the present disclosure that will be effective in the protection against acetaminophen-induced liver injury can be determined by standard clinical techniques. In addition, in vitro or in vivo assays can optionally be employed to help identify optimal dosage ranges. The precise dose to be employed will also depend on the route of administration, and can be decided according to the judgment of the practitioner and each patient's circumstances. However, suitable dosage ranges for oral administration can generally be about 0.001 milligram to about 400 milligrams of a chemical of the present disclosure or a pharmaceutically acceptable salt thereof per kilogram body weight per day. In specific preferred embodiments of the disclosure, the oral dose is about 0.01 milligram to about 100 milligrams per kilogram body weight per day, or about 0.1 milligram to about 75 milligrams per kilogram body weight per day. The dosage amounts described herein refer to total amounts administered; that is, if more than one chemical of the present disclosure is administered, or if a chemical of the present disclosure is administered with a therapeutic agent, then the preferred dosages correspond to the total amount administered. Oral compositions can contain about 10% to about 95% active ingredient by weight.

The dosage of acetaminophen can be about 50 mg, about 75 mg, about 100 mg, about 125 mg, about 150 mg, about 200 mg, about 225 mg, about 250 mg, about 275 mg, about 300 mg, about 325 mg, about 350 mg, advantageously about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 2600 mg, about 2700 mg, about 2800 mg, about 2900 mg, about 3000 mg, about 3100 mg, about 3200 mg, about 3300 mg, about 3400 mg, about 3500 mg, about 3600 mg, about 3700 mg, about 3800 mg, about 3900 mg or about 4000 mg.

The dosage of vitamin U can be about 50 mg, about 75 mg, about 100 mg, about 125 mg, about 150 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 2600 mg, about 2700 mg, about 2800 mg, about 2900 mg, about 3000 mg, about 3100 mg, about 3200 mg, about 3300 mg, about 3400 mg, about 3500 mg, about 3600 mg, about 3700 mg, about 3800 mg, about 3900 mg or about 4000 mg.

The dosage of vitamin U can be about 4100 mg, about 4200 mg, about 4300 mg, about 4400 mg, about 4500 mg, about 4600 mg, about 4700 mg, about 4800 mg, about 4900 mg, about 5000 mg, about 5100 mg, about 5200 mg, about 5300 mg, about 5400 mg, about 5500 mg, about 5600 mg, about 5700 mg, about 5800 mg, about 5900 mg, about 6000 mg, about 6100 mg, about 6200 mg, about 6300 mg, about 6400 mg, about 6500 mg, about 6600 mg, about 6700 mg, about 6800 mg, about 6900 mg, about 7000 mg, about 7100 mg, about 7200 mg, about 7300 mg, about 7400 mg, about 7500 mg, about 7600 mg, about 7700 mg, about 7800 mg, about 7900 mg, about 8000 mg, about 8100 mg, about 8200 mg, about 8300 mg, about 8400 mg, about 8500 mg, about 8600 mg, about 8700 mg, about 8800 mg, about 8900 mg or about 9000 mg.

The dosage of vitamin U can be about 9100 mg, about 9200 mg, about 9300 mg, about 9400 mg, about 9500 mg, about 9600 mg, about 9700 mg, about 9800 mg, about 9900 mg, about 11000 mg, about 11100 mg, about 11200 mg, about 11300 mg, about 11400 mg, about 11500 mg, about 11600 mg, about 11700 mg, about 11800 mg, about 11900 mg, about 12000 mg, about 12100 mg, about 12200 mg, about 12300 mg, about 12400 mg, about 12500 mg, about 12600 mg, about 12700 mg, about 12800 mg, about 12900 mg, about 13000 mg, about 13100 mg, about 13200 mg, about 13300 mg, about 13400 mg, about 13500 mg, about 13600 mg, about 13700 mg, about 13800 mg, about 13900 mg, about 14000 mg, about 15100 mg, about 15200 mg, about 15300 mg, about 15400 mg, about 15500 mg, about 15600 mg, about 15700 mg, about 15800 mg, about 15900 mg or about 16000 mg.

The dosage of vitamin U can be about 16100 mg, about 16200 mg, about 16300 mg, about 16400 mg, about 16500 mg, about 16600 mg, about 16700 mg, about 16800 mg, about 16900 mg, about 17000 mg, about 17100 mg, about 17200 mg, about 17300 mg, about 17400 mg, about 17500 mg, about 17600 mg, about 17700 mg, about 17800 mg, about 17900 mg, about 18000 mg, about 18100 mg, about 18200 mg, about 18300 mg, about 18400 mg, about 18500 mg, about 18600 mg, about 18700 mg, about 18800 mg, about 18900 mg, about 19000 mg, about 19100 mg, about 19200 mg, about 19300 mg, about 19400 mg, about 19500 mg, about 19600 mg, about 19700 mg, about 19800 mg, about 19900 mg or about 20000 mg.

The dosage of cystine can be about 50 mg, about 75 mg, about 100 mg, about 125 mg, about 150 mg, about 200 mg, about 225 mg, about 250 mg, about 275 mg, about 300 mg, about 325 mg, about 350 mg, advantageously about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 2600 mg, about 2700 mg, about 2800 mg, about 2900 mg, about 3000 mg, about 3100 mg, about 3200 mg, about 3300 mg, about 3400 mg, about 3500 mg, about 3600 mg, about 3700 mg, about 3800 mg, about 3900 mg or about 4000 mg.

The dosage of cystine can be about 4100 mg, about 4200 mg, about 4300 mg, about 4400 mg, about 4500 mg, about 4600 mg, about 4700 mg, about 4800 mg, about 4900 mg, about 5000 mg, about 5100 mg, about 5200 mg, about 5300 mg, about 5400 mg, about 5500 mg, about 5600 mg, about 5700 mg, about 5800 mg, about 5900 mg, about 6000 mg, about 6100 mg, about 6200 mg, about 6300 mg, about 6400 mg, about 6500 mg, about 6600 mg, about 6700 mg, about 6800 mg, about 6900 mg, about 7000 mg, about 7100 mg, about 7200 mg, about 7300 mg, about 7400 mg, about 7500 mg, about 7600 mg, about 7700 mg, about 7800 mg, about 7900 mg, about 8000 mg, about 8100 mg, about 8200 mg, about 8300 mg, about 8400 mg, about 8500 mg, about 8600 mg, about 8700 mg, about 8800 mg, about 8900 mg or about 9000 mg.

The dosage of cystine can be about 9100 mg, about 9200 mg, about 9300 mg, about 9400 mg, about 9500 mg, about 9600 mg, about 9700 mg, about 9800 mg, about 9900 mg, about 11000 mg, about 11100 mg, about 11200 mg, about 11300 mg, about 11400 mg, about 11500 mg, about 11600 mg, about 11700 mg, about 11800 mg, about 11900 mg, about 12000 mg, about 12100 mg, about 12200 mg, about 12300 mg, about 12400 mg, about 12500 mg, about 12600 mg, about 12700 mg, about 12800 mg, about 12900 mg, about 13000 mg, about 13100 mg, about 13200 mg, about 13300 mg, about 13400 mg, about 13500 mg, about 13600 mg, about 13700 mg, about 13800 mg, about 13900 mg, about 14000 mg, about 15100 mg, about 15200 mg, about 15300 mg, about 15400 mg, about 15500 mg, about 15600 mg, about 15700 mg, about 15800 mg, about 15900 mg or about 16000 mg.

The dosage of cystine can be about 16100 mg, about 16200 mg, about 16300 mg, about 16400 mg, about 16500 mg, about 16600 mg, about 16700 mg, about 16800 mg, about 16900 mg, about 17000 mg, about 17100 mg, about 17200 mg, about 17300 mg, about 17400 mg, about 17500 mg, about 17600 mg, about 17700 mg, about 17800 mg, about 17900 mg, about 18000 mg, about 18100 mg, about 18200 mg, about 18300 mg, about 18400 mg, about 18500 mg, about 18600 mg, about 18700 mg, about 18800 mg, about 18900 mg, about 19000 mg, about 19100 mg, about 19200 mg, about 19300 mg, about 19400 mg, about 19500 mg, about 19600 mg, about 19700 mg, about 19800 mg, about 19900 mg or about 20000 mg.

When administered to a patient, acetaminophen and one chemical of the present disclosure, for example, SMM, are preferably administered as components of a composition that optionally comprises a pharmaceutically acceptable vehicle. The compositions of the present disclosure can be administered orally. The compositions of the present disclosure can be administered by any other convenient route, for example, by infusion or bolus injection, by absorption through epithelial or mucocutaneous linings (e.g., oral mucosa, rectal, and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer the compositions of the present disclosure.

In some embodiments, the compositions can comprise acetaminophen and one or more chemicals of the present disclosure.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of chemicals of the present disclosure into the bloodstream.

In an advantageous embodiment, the administration is oral.

Compositions of the present disclosure can optionally comprise a suitable amount of a pharmaceutically acceptable vehicle so as to provide a form for proper administration to a patient.

In a specific embodiment, the term "pharmaceutically acceptable" can mean approved by a regulatory agency of the Federal or a state government or listed in the U.S. Pharmacopeia or other generally recognized pharmacopeia for use in animals, mammals, and more particularly in humans. The term "vehicle" can refer to a diluent, adjuvant, excipient, or carrier with which a compound of the disclosure is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a patient, the pharmaceutically acceptable vehicles are preferably sterile. Water is a preferred vehicle when the compound of the disclosure is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or buffering agents.

The pharmaceutically acceptable compositions of present disclosure can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698, 155). Other examples of suitable pharmaceutical vehicles are described in Remington's Pharmaceutical Sciences, Alfonso R. Gennaro ed., Mack Publishing Co. Easton, Pa., 19th ed., 1995, pp. 1447 to 1676, incorporated herein by reference.

The pharmaceutically acceptable compositions of present disclosure are preferably administered in the form of a caplet or a tablet or a capsule. A tablet generally refers to a small solid pill containing a measured medicinal dose, usually intended to be taken orally. A caplet generally refers to a tablet of medicine taken orally. The terms tablet and caplet can be used interchangeably. The tablet or caplet can contain a liquid gel, a rapid release or extended release version of any of the herein disclosed formulations.

A capsule is a gelatinous envelope enclosing the active substance. Capsules can be designed to remain intact for some hours after ingestion in order to delay absorption. They can also contain a mixture of slow- and fast-release particles to produce rapid and sustained absorption in the same dose.

In a preferred embodiment, the compounds of the disclosure are formulated in accordance with routine procedures as a pharmaceutical composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, etc. Such vehicles are preferably of pharmaceutical grade. Typically, compositions for intravenous administration comprise sterile isotonic aqueous buffer. Where necessary, the compositions can also include a solubilizing agent.

The caplet or tablet or capsule or liquid suspension can further comprise artificial colors, calcium carbonate salts, calcium phosphate salts, carboxymethylcellulose, carnauba wax, cellulose, corn starch, croscarmallose sodium, hydroxypropylcellulose, iron oxide, magnesium stearate, mannitol, methylcellulose, microcrystalline cellulose, polyethylene glycol, polyvinyl alcohol, polyvinylpolypyrillidone, polyvinylpyrillidone, silicon dioxide, sodium starch glycolate, sorbitol, stearic acid, sucralose, talc, titanic dioxide and xylitol or any combination thereof. Preferably, the caplet or tablet does not contain gluten, preservatives, sugar, sodium, milk, yeast, artificial colors, artificial flavors or any combination thereof.

Advantageously, the caplet or tablet can be enteric coated and can further comprise anionic polymers of methacrylic acid, artificial colors, calcium carbonate salts, calcium phosphate salts, carboxymethylcellulose, carnauba wax, cellulose, cellulose derivatives, corn starch, croscarmallose sodium, glycerol monostearate, hydroxypropylcellulose, iron oxide, magnesium stearate, mannitol, methacrylates, methyl vinyl ether derivatives, methylcellulose, methylphalates, microcrystalline cellulose, polyethylene glycol, polymethacrylates, polyvinyl alcohol, polyvinylpolypyrillidone, polyvinylpyrillidone, silicon dioxide, sodium acetate phalate, sodium starch glycolate, sorbitol, stearic acid, sucralose, talc, titanic dioxide and xylitol or any combination thereof.

In another advantageous embodiment, the caplet or tablet or capsule can be a controlled release of the active acetaminophen to allow about 6, 8, or 12 hours or more of pain or fever relief. The controlled release caplet or caplet can comprise anionic polymers of methacrylic acid, artificial colors, calcium carbonate salts, calcium phosphate salts, carboxymethylcellulose, carnauba wax, cellulose, cellulose derivatives, corn starch, croscarmallose sodium, diglycerides, ethylcellulose, fatty acid esters, glycerol monostearate, gum (e.g., xanthan), hydroxypropylcellulose, iron oxide, magnesium stearate, mannitol, methacrylates, methyl vinyl ether derivatives, methylcellulose, methylphalates, microcrystalline cellulose, monoglycerides, polyethylene glycol, polymethacrylates, polyvinyl alcohol, polyvinylpolypyrillidone, polyvinylpyrillidone, silicon dioxide, sodium acetate phalate, sodium starch glycolate, sorbitol, stearex, stearic acid, sucralose, talc, titanic dioxide, wax (e.g., carnuba) and xylitol or any combination thereof.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to about 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

What is claimed is:

1. A pharmaceutical composition comprising: an effective amount of acetaminophen and an effective amount of one or more components chosen from S-adenosylhomocysteine (SAH), S-methylmethionine (SMM), or a pharmaceutically acceptable salt thereof.

2. The composition of claim 1, wherein the component is S-adenosylhomocysteine (SAH).

3. The composition of claim 1, wherein the component is S-methylmethionine (SMM).

4. The composition of claim 1, wherein the composition consists essentially of: an effective amount of acetaminophen and an effective amount of one or more components chosen from S-adenosylhomocysteine (SAH), S-methylmethionine (SMM), or a pharmaceutically acceptable salt thereof.

5. The composition of claim 4, wherein the component is S-adenosylhomocysteine (SAH).

6. The composition of claim 4, wherein the component is S-methylmethionine (SMM).

7. The composition of claim 1, wherein the composition consists of: an effective amount of acetaminophen and an effective amount of one or more components chosen from S-adenosylhomocysteine (SAH), S-methylmethionine (SMM), or a pharmaceutically acceptable salt thereof.

8. A method of reducing acetaminophen-induced liver toxicity in a subject comprising administering or co-administering an effective amount of one or more components chosen from S-adenosylhomocysteine (SAH), S-methylmethionine (SMM), or a pharmaceutically acceptable salt thereof, with an effective amount of acetaminophen to a subject.

9. The method of claim 8, wherein the component is S-adenosylhomocysteine (SAH).

10. The method of claim 8, wherein the component is S-methylmethionine (SMM).

11. A pharmaceutical composition comprising: a pharmaceutically acceptable carrier and a pharmaceutically effective amount of a composition comprising: acetaminophen and one or more components chosen from S-adenosylhomocysteine (SAH), S-methylmethionine (SMM), or a pharmaceutically acceptable salt thereof.

* * * * *